United States Patent [19]  [11]  4,042,635
Rys et al.  [45]  Aug. 16, 1977

[54] SPIRO COMPOUNDS

[75] Inventors: Paul Rys, Zurich; Rolf Vogelsanger, Zumikon, both of Switzerland

[73] Assignee: Ciba-Geigy Corporation, Ardsley, N.Y.

[21] Appl. No.: 638,573

[22] Filed: Dec. 8, 1975

Related U.S. Application Data

[62] Division of Ser. No. 528,620, Dec. 2, 1974, Pat. No. 3,950,403.

[30] Foreign Application Priority Data

July 28, 1971  Switzerland ..................... 11176/71

[51] Int. Cl.² ............................................. C07C 39/26

[52] U.S. Cl. ................................................ 260/623 D
[58] Field of Search ........................ 260/623 D, 623 R Primary Examiner—James O. Thomas, Jr.
Assistant Examiner—W. B. Lone
Attorney, Agent, or Firm—Karl F. Jorda; Edward McC. Roberts; Prabodh I. Almaula

[57] ABSTRACT

Compounds which contain a group bonded directly to an aromatic nucleus of the formula $$-(CH_2-)_n-X \quad (1)$$

in which $n$ is a positive integer having a value of at least 2 and X represents a removable substituent.

2 Claims, No Drawings

SPIRO COMPOUNDS

This is a divisional of application Ser. No. 528,620, filed on Dec. 2, 1974 now U.S. Pat. No. 3,950,403.

The invention relates to spiro compounds with dyestuff character, and to compounds which are suitable for the manufacture of such spiro compounds and which contain an aliphatic group, directly bonded to an aromatic nucleus, which possesses a removable substituent, especially a group of the formula $$-(CH_2)_n-X \qquad (1)$$

wherein $n$ denotes a positive integer having a value of at least 2 and X denotes a removable substituent.

Amongst the starting compounds which are suitable for the manufacture of spiro compounds according to the invention, particular interest attaches to those which contain a group of the formula (1), which is directly bonded to an aromatic nucleus of an at least bicyclic aromatic six-membered ring system, and wherein $n$ denotes a positive integer having a value of at least 2 and X denotes a halogen atom, an acyloxy or sulphato, thiosulphato or tosylate group or a quaternary ammonium group. These starting compounds can themselves possess dyestuff character, or they can be converted into compounds with dyestuff character, for example by coupling, acylation or the like. The number $n$ is preferably less than 10, for example 4 or 5.

Important compounds of the type described above are above all those which contain a grouping of the formula (1), wherein $n = 2$.

As an example, there may especially be mentioned compounds which correspond to the formula

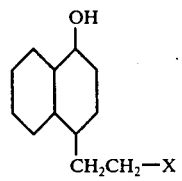

(2)

wherein X represents a chlorine or bromine atom, or compounds which contain a radical of the formula (2), which is bonded to another radical, for example via an azo, amino, carbonyl, oxycarbonyl, aminocarbonyl, sulphonyl or sulphamino bridge or the like.

In this case either the other radical to which the radical of the formula (2) is bonded is a chromogen, or only both radicals together form a dyestuff, such as, for example, in the azo series. The ring system of the formula (2) can contain further substituents, such as, for example, halogen atoms, amino, nitro, sulphonic acid, carboxyl, sulphonyl, sulphonamino, alkyl, aryl, alkoxy, aryloxy, acyl and acylamino groups and the like. Preferably, however, the compounds of the formula (2) or the radical of the formula (2) are unsubstituted.

The corresponding spiro compounds can be manufactured from the naphthalene derivatives of the formula (2) by treatment with sodium hydroxide solution, for example in ether or acetone, in which case, hydrogen halide is split off and cyclisation to give the spirodienone of the formula

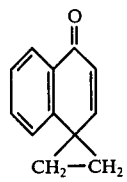

(3)

occurs, or a compound is formed which contains a radical of the formula (3). As regards bonding to another radical, or possible further substituents, the same applies here as has been said in the elucidation of the formula (2).

Compounds of the formula (2), for example of 1-hydroxy-4-($\beta$-iodoethyl)-naphthalene, can be manufactured by reacting $\alpha$-naphthol with ethylene oxide in the presence of aluminium chloride and subsequently reacting the resulting 1-($\beta$-hydroxyethoxy)-4-($\beta$-hydroxyethyl)-naphthalene with hydrogen iodide. In another method of manufacture, $\alpha$-naphthol again serves as the starting substance. It is nitrated with nitric acid to give 4-nitro-naphthol-(1), which is then reduced by means of hydrogen/platinum catalyst to give 4-amino-naphthol-(1). The resulting product is converted into the corresponding zinc chloride adduct by means of metallic zinc and hydrochloric acid in tetrahydrofurane, and the 1.4-diazoxide is finally obtained from the adduct by diazotisation with sodium nitrite and hydrochloric acid. The 1,4-diazoxide is now converted by photolysis in the presence of an olefine into the corresponding spirodienone, the irradiation being carried out through potassium chromate/dichromate solution as a filter, so as to absorb radiation of undesired wavelengths and thus prevent direct activation of the photolabile spirodienone produced. The progress of the reaction can be seen from the evolution of nitrogen or the disappearance of the orange diazoxide colour. Ethylene may especially be mentioned as an olefine which can be used in this process. The spirodienone obtained can be freed of the excess olefine by concentration and be purified by recrystallisation from cold pentane. Reaction of the spirodienone obtained [of the type of the formula (3)] with a hydrogen halide acid, for example hydrogen bromide or hydrogen iodide, opens the ring produced by condensation with the olefine, and the desired 1-hydroxy-4-($\omega$-halogenalkyl)-naphthalene is produced. Both the methods described furnish the end product in good yields. A further, new method is described in the embodiment of the Example 1.

The linkage of compounds of the formulae (2) or (3) to other radicals which either by themselves already possess dyestuff character or together with the radical of the formula (2) or (3) form a compound with dyestuff character can be carried out in various ways.

Thus it is, for example, possible to convert 1-methoxy-4-($\beta$-hydroxyethyl)-naphthalene, by nitration with nitric acid at 0° C, into 1-methoxy-2-nitro-4-($\beta$-hydroxyethyl)-naphthalene, and to convert this, by reaction with hydrogen iodide, into 2-nitro-4-($\beta$-iodoethyl)-naphthol-(1), to convert this, by reduction with hydrogen in the presence of Raney nickel in ethanol, into the corresponding 2-amino compound, and finally to convert the latter, by condensation with a sulphochloride possessing dyestuff character, into a dyestuff of the formula

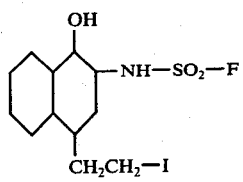

Possible radicals F are, for example, those of the anthraquinone, phthalocyanine or azo series, or the like.

According to another method, 1-hydroxy-4-(β-chlorosulphatoethyl)-naphthalene-2-sulphochloride can be obtained by reacting, for example, 1-hydroxy-4-(β-hydroxyethyl)-naphthalene with chlorosulphonic acid in carbon tetrachloride, and the product can then be reacted with an amine which possesses dyestuff character, to form the corresponding naphthalene-sulphonic acid amide. Here again the chromophoric radical of the amine can belong to the most diverse classes of dyestuffs.

A particularly interesting class of the compounds according to the invention are the azo dyestuffs of the general formula

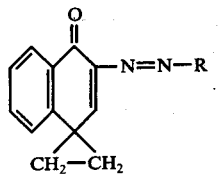

wherein R denotes a radical of the benzene or naphthalene series, which are, for example, obtained from 4-(β-halogenoethyl naphthol-(1) by coupling with an appropriate diazotized amine, and subsequent removal of hydrogen halide. When acting on cellulose fibres, the three-membered ring reacts with the hydroxyl groups of the cellulose to open the ring and form a stable ether bridge to the cellulose molecule.

The spiro compounds according to the invention, possessing dyestuff character, the compounds of the formulae (2) and (3), and the compounds possessing dyestuff character which contain a radical of the formula (2) or (3), are new. They possess the property of fibre reactivity, that is to say they are capable of forming covalent chemical bonds with the hydroxyl groups of cellulose or the amino groups of polyamides.

They are therefore suitable for dyeing and printing the most diverse materials such, for example, as silk, leather, wool, synthetic fibres from polyamides or polyurethanes, and polyhydroxylic materials such, for example, as cellulose-containing materials of fibrous structure, such as linen, staple rayon, regenerated cellulose, cotton and the like.

The most important compounds according to the invention are those which contain a water-solubilizing group, especially a sulphonic acid group. These dyestuffs are preferably used for dyeing nitrogenous fibres such, for example, as polyamides, polyurethanes, silk, leather, and especially wool, for example from a weakly acid, neutral or weakly alkaline bath, optionally with the addition of the customary assistants, for example ethylene oxide condensation products of high molecular amines, and for dyeing cellulose materials, especially cotton, for example by the exhaustion process from a dilute liquor, from an alkaline aqueous bath which optionally has a high salt content, and especially by the pad dyeing process, in which the goods are impregnated with aqueous dyestuff solutions which optionally also contain salt, and the dyestuffs are fixed after an alkaline treatment or in the presence of alkali, if appropriate accompannied by a heat treatment.

The reactive dyestuffs according to the invention are fixed on cotton in a weakly acid to alkaline solution, and on wool and synthetic polyamides, preferably in an acid medium.

Because of the stability of the fibre-dyestuff bond produced by the reactive radical, the dyeings obtained with the new dyestuffs on the materials mentioned yield excellent fastness properties, especially wet fastness properties.

To improve the wet fastness properties it is advisable to subject the dyeings and prints obtained to a thorough rinse with cold and hot water, optionally with the addition of an agent which has a dispersing action and assists the diffusion of the non-fixed material.

The water-soluble reactive dyestuffs according to the invention are also suitable for printing, for example on cotton but also for printing nitrogen-containing fibres, for example wool, silk or mixed fabrics containing wool.

In the examples which follow, the parts, unless otherwise stated, denote parts by weight and the percentages denote percentages by weight. The relationship of parts by weight to parts by volume is the same as of the gram to the cubic centimeter.

EXAMPLE 1

322 g of 1-naphthol are rapidly treated with 1.44 liter of 10% strength potassium hydroxide solution in a four-necked flask, whilst stirring. 280 g of dimethyl sulphate are now added dropwise from a dropping funnel, whilst cooling with ice water, in such a way that the temperature remains below 40° C. The dark red reaction mixture is thereafter heated on a boiling water bath for 30 minutes. After cooling, the dark organic phase is separated off, the aqueous phase is extracted with ether, the two organic phases are combined, washed with 2 N potassium hydroxide solution and water and dried over calcium chloride, and the solvent is distilled off on a rotary evaporator. The reaction product is purified by distillation in a high vacuum.

264.8 g of the 1-methoxy-naphthalene obtained are dissolved in 400 ml of carbon tetrachloride and introduced into a 2 liter five-necked flask with stirrer, thermometer, gas inlet tube, condenser and dropping funnel. A solution of 283 g of bromine in 130 ml of carbon tetrachloride is now slowly added dropwise over the course of 6 hours in such a way that the temperature does not exceed 0° C (cooling by means of an ice/sodium chloride bath). In order to ensure expulsion of the hydrogen bromide produced, a slight stream of dry nitrogen is bubbled through the reaction mixture during the addition of the bromine, and subsequently overnight.

The clear yellow solution is then washed with water containing bisulphite (10 g of sodium bisulphite in 600 ml of water) extracted by shaking three times with 300 ml of dilute potassium hydroxide solution and ice in each case, washed repeatedly with water and freed of the solvent on a rotary evaporator, and the residue is distilled in a high vacuum.

238.5 g of the 1-bromo-4-methoxy-naphthalene obtained are dissolved in 200 ml of diethyl ether and introduced into a 3 liter five-neck flask. 31 g of magnesium filings which have been washed with ether, dried for 24 hours in a high vacuum and warmed in a closed flask with 200 mg of iodine over a flame, are then added. A mixture of 38 g of ethylene bromide, 50 ml of diethyl ether, 150 ml of benzene and 10 ml of freshly distilled methyl iodide is now slowly added dropwise over the course of 20 hours from a Hershberg dropping funnel, in the course of which the bath temperature should initially be 55° C, and 75° C after 5 hours and up to the end of the addition.

After completion of the addition, the reaction solution is cooled to 0° C. 53 g of ethylene oxide are now added to 250 ml of diethyl ether cooled to −50° C, and this solution is added dropwise to the Grignard reagent, with vigorous stirring, in such a way that the temperature is about 0° C (cooling with an ice/sodium chloride bath), whereupon a yellow precipitate is produced. After completion of the addition the mixture is further stirred until room temperature is reached, and is subsequently boiled for 1 hour under reflux.

150 ml of concentrated sulphuric acid in 1 liter of ice/water are then slowly added while cooling strongly, whereupon the precipitate dissolves completely and the temperature rises somewhat despite the cooling. The yellow organic phase is now separated off, the aqueous phase is extracted with ether, the combined organic phases are washed 3 times with 1 liter of 5% strength potassium hydroxide solution at a time, repeatedly washed with water and dried with 200 g of anhydrous sodium carbonate. Finally, the solvents are distilled off on a rotary evaporator, and the oil, which shows a blue-green iridescence, is distilled under a high vacuum.

100 g of the β-4-methoxy-1-naphthyl-ethyl-alcohol obtained are dissolved in 3 liters of glacial acetic acid. 400 ml of concentrated hydriodic acid (57% strength), which has been freshly distilled, are added. The solution is heated to the boil (110° C), whereupon a mixture of methyl iodide/water/acetic acid is evolved. At the same time, a vigorous stream of nitrogen is passed through the reaction mixture, but care must be taken to periodically replace the acetic acid evolved, so that excessively high concentrations of the adduct and product do not build up. After 2 hours, the reaction is complete. The hot reaction solution is filtered and treated with 10 g of sodium bisulphite in 2 liters of water, whereupon the product precipitates. The product is recrystallized from benzene/carbon tetrachloride or from ethanol/water.

3.24 g of 2-naphthylamine-5,7-disulphonic acid (sodium salt) are dissolved in 5 ccs of concentrated hydrochloric acid and 100 ml of water. 10 ml of sodium nitrite solution are added dropwise to the solution cooled to 0° C.

2.98 g of β-4-hydroxy-1-naphthyl-ethyl iodide are dissolved in 200 ml of methanol, and the acid solution of the diazo component described above is added thereto. The $p_H$ of the reaction solution is adjusted to 6.5 by careful addition of 5% strength sodium hydroxide solution. The dyestuff of the formula

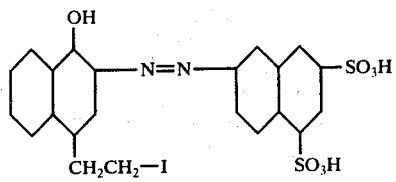

has completely formed after 2 hours, and can be isolated by salting-out. (To avoid exceeding the critical $p_H$ value of 7, 0.5% strength sodium hydroxide solution is used towards the end of the addition of the sodium hydroxide).

The β-4-methoxy-1-naphthyl-ethyl alcohol used as intermediate product for manufacturing the β-4-hydroxy-1-naphthylethyl iodide can also be obtained as follows:

60 ml of solvent (preferably 1,2-dichloroethane or benzene) are treated with 17 g of powdered aluminum chloride in a 1-l three-necked flask fitted with stirrer, dropping funnel, and reflux cooler with calcium chloride tube, and 10 g of 1-methoxynaphthalene are added dropwise while stirring and cooling with ice water. While stirring thoroughly, a solution consisting of 640 ml of solvent (preferably 1,2-dichloroethane or benzene) and 5.4 g of ethylene oxide is subsequently added in such a way that the internal temperature remains constant at approx. 20° C. Upon completion of the addition, the reaction mixture is poured on a mixture of 1 kg of ice and 100 ml of concentrated hydrochloric acid. The organic phase is isolated, washed with water until neutral, dried over sodium sulphate and the solvent is distilled off. The residual crude product can be recrystallized from n-hexane/chloroform = 20/1. The resulting β-4-methoxy-1-naphthyl-ethyl alcohol has a melting point of 86° – 87° C.

EXAMPLE 2

10 g of β-4-hydroxy-1-naphthyl-ethyl iodide are dissolved in 250 ml of ether and introduced into a separating funnel. 250 ml of 2 N sodium hydroxide solution are added thereto and the two phases are vigorously shaken for 15 minutes. The ether phase is now separated off and dried with calcined sodium carbonate, and the ether is distilled off on a rotary evaporator. The crude product which remains can be recrystallized from ether/ligroin. The benzo[d]-spiro-[2,5]-octa-1,4-dien-3-one obtained corresponds to the formula

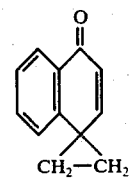

and shows a melting point of 97° – 98° C.

Dyeing Instruction for Cotton 20 g of woven cotton fabric are introduced into a solution which contains 0.6 g of dyestuff dissolved in 500 ml of water. The liquor is then rendered alkaline with dilute sodium hydroxide solution, up to a $p_H$ value of at most 11.5. After 15 minutes, 50 g of sodium chloride are added and dissolved whilst warming the liquor to 50° C. The dyeing solution is kept for 1 hour at 50° C.

The fabric is then squeezed out and dried for 5 minutes at 120° C. A fast dyeing results.

Equally good dyeing results can be achieved if the 5 minutes' drying is omitted.

By dyestuffs are to be understood in this context the 4-(β-X-ethylnaphth-(1)-ols, for example of the formula

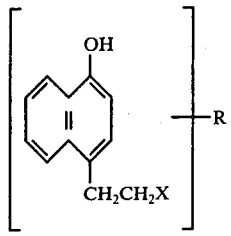

and the corresponding spiro compounds, for example of the formula

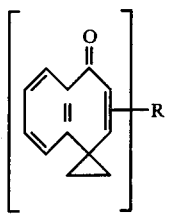

Dyeing Instruction for Wool

A solution containing 0.6 g of a dyestuff of the general formula

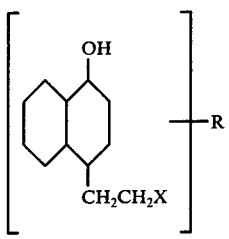

in which X represents a chlorine, bromine or iodine atom or a quaternary ammonium group and R represents an aromatic radical, dissolved in 500 ml of water, is rendered alkaline (pH 12) with dilute sodium hydroxide solution. After 90 minutes, the solution is acidified to pH 8 with glacial acetic acid. 20 Grams of wool fabric are then introduced into this bath, which is adjusted to pH 4 to 5 by adding further glacial acetic acid. 50 Grams of sodium chloride are then added and the bath heated to 30° C. After 30 minutes, the fabric is squeezed out at 30° C and dried for 15 minutes at 60° C.

Equally good dyeing results can be attained if the 15 minutes drying is omitted.

If the corresponding spiro compound is used as dyestuff, the solution is not rendered alkaline before the fabric is added.

EXAMPLE 3

10 Grams of β-4-hydroxy-1-naphthyl-ethyl chloride are dissolved in 300 ml of chloroform and the solution is cooled to 0° C. Chlorosulphonic acid is dropwise added thereto, the temperature of the reaction mixture being kept preferably at 0° to 5° C. Upon completion of the addition, the reaction mixture is heated to room temperature within 30 minutes, then poured on ice. The chloroform phase is isolated, dried with sodium carbonate and the chloroform distilled off. The residual crude product can be recrystallised from n-hexane. The resulting product corresponds to the formula

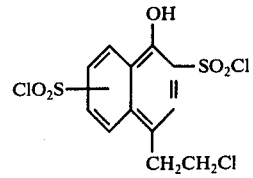

and has a melting point of 126° – 127° C.

The equimolar amount of the above described sulphochloride is introduced in small amounts into a solution of the compound of the formula

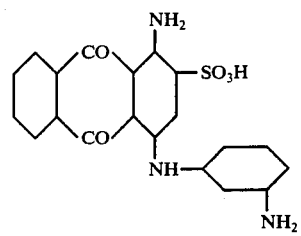

in pyridine, whilst stirring and at room temperature. Upon completion of the reaction, the pyridine is distilled off. The residual product is dissolved in water, then treated with an equal amount of ethyl alcohol and filtered. The reactive dyestuff is obtained by salting it out from the filtrate with sodium chloride.

EXAMPLE 4

The compound of the formula

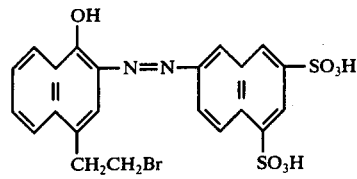

(instead of which the corresponding spiro compound can also be used) is dissolved in water and treated with 1 to 5 times the equimolar amount of potassium cyanide at 0° to 60° C. After 1 to 30 minutes the compound of the formula

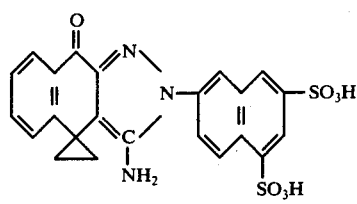

precipitates (optionally, only after concentrating) from the reaction mixture and can be filtered off.

In methanol as solvent, the compound of the formula

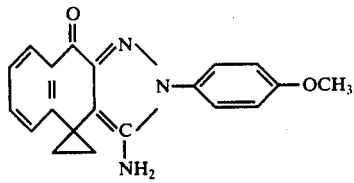

having a decomposition point of 250° to 252° C, is likewise obtained from the compound of the formula

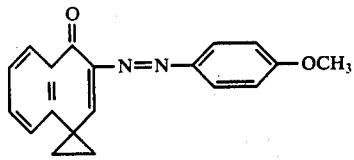

If the two above described heterocyclic spiro compounds are diazotised and coupled to the 2-hydroxy-naphthalene-3,6-disulphonic acid, red dyestuffs are obtained.

We claim:

1. A compound which contains a group of the formula, $$-(CH_2)_n-X \qquad (1)$$

which is bonded directly to an aromatic nucleus of an at least bicyclic, aromatic six-membered naphthalene ring system, wherein $n$ is a positive integer havng a value of 2 and X represents a halogen atom.

2. A compound according to claim 1, wherein $n = 2$.

* * * * *